(12) United States Patent
Weedon et al.

(10) Patent No.: US 9,722,429 B2
(45) Date of Patent: Aug. 1, 2017

(54) POWER DELIVERY TO A MOVING UNIT

(75) Inventors: Hans J. Weedon, Salem, MA (US);
Stephen Quigley, E Hampstead, NH (US)

(73) Assignee: ANALOGIC CORPORATION, Peabody, MA (US)

( * ) Notice: Subject to any disclaimer, the term of this patent is extended or adjusted under 35 U.S.C. 154(b) by 678 days.

(21) Appl. No.: 14/348,009

(22) PCT Filed: Sep. 30, 2011

(86) PCT No.: PCT/US2011/054276
§ 371 (c)(1),
(2), (4) Date: Mar. 27, 2014

(87) PCT Pub. No.: WO2013/048445
PCT Pub. Date: Apr. 4, 2013

(65) Prior Publication Data
US 2014/0239715 A1    Aug. 28, 2014

(51) Int. Cl.
*A61B 6/03*    (2006.01)
*H01F 38/18*    (2006.01)
(Continued)

(52) U.S. Cl.
CPC ............... *H02J 4/00* (2013.01); *A61B 6/56* (2013.01); *H01F 38/18* (2013.01); *H02J 5/005* (2013.01);
(Continued)

(58) Field of Classification Search
CPC ....... A61B 6/032; A61B 6/035; A61B 6/4435; A61B 6/56; H01F 38/18; H02J 5/005;
(Continued)

(56) References Cited

U.S. PATENT DOCUMENTS 4,225,851 A * 9/1980 Reschovsky ......... G01D 18/006
340/870.04
4,628,426 A 12/1986 Steigerwald
(Continued)

FOREIGN PATENT DOCUMENTS

CN    101026033 A    8/2007
CN    101632141 A    1/2010
(Continued)

OTHER PUBLICATIONS

First Chinese Office Action cited in Chinese Application No. 201180072782.6 dated Nov. 29, 2015, 8 pgs.
(Continued)

*Primary Examiner* — Levi Gannon
(74) *Attorney, Agent, or Firm* — Cooper Legal Group, LLC

(57) ABSTRACT

Power delivery of an image modality system for transferring power from a transmission unit (e.g., stationary unit) to a reception unit (e.g., a moving and/or rotating unit). A modulated electric signal comprising at least two modulated characteristics (e.g., such as amplitude and frequency) is configured to (e.g., concurrently) supply power to both high voltage and lower voltage components (216, 222) of the reception unit. An auxiliary component (316) is configured to utilize a first of the modulated characteristics (e.g., amplitude) to adjust/regulate a voltage applied to the lower voltage component (s), and a filter component (324) (e.g., such as a frequency selective circuit) is configured to utilize a second of the modulated characteristics (e.g., frequency) to adjust/regulate a voltage applied to the high voltage component (s).

20 Claims, 4 Drawing Sheets

(51) Int. Cl.
*H02J 5/00* (2016.01)
*H02J 4/00* (2006.01)
*H02J 50/10* (2016.01)
*A61B 6/00* (2006.01)
*H02M 1/00* (2006.01)

(52) U.S. Cl.
CPC .............. *H02J 50/10* (2016.02); *A61B 6/035* (2013.01); *A61B 6/4435* (2013.01); *H02M 2001/009* (2013.01); *Y10T 307/297* (2015.04)

(58) Field of Classification Search
CPC .... H02J 17/00; H02J 50/10; H02M 2001/009; H05G 1/10; H05G 1/12; Y10T 307/25; Y10T 307/297
USPC .......................... 307/17, 104; 378/101, 104
See application file for complete search history.

(56) References Cited

U.S. PATENT DOCUMENTS

| | | | | |
|---|---|---|---|---|
| 5,438,496 A | * | 8/1995 | Meur | H01F 38/14 363/16 |
| 5,455,466 A | * | 10/1995 | Parks | H02J 7/025 307/104 |
| 5,742,515 A | * | 4/1998 | Runkle | H01F 38/18 290/40 C |
| 7,054,411 B2 | * | 5/2006 | Katcha | H05G 1/10 336/105 |
| 7,197,113 B1 | | 3/2007 | Katcha et al. | |
| 7,957,786 B2 | * | 6/2011 | Katcha | A61B 6/56 336/145 |
| 8,571,179 B2 | * | 10/2013 | Beland | H05G 1/10 378/101 |
| 2006/0280289 A1 | | 12/2006 | Hanington et al. | |
| 2007/0195924 A1 | * | 8/2007 | Krumme | A61B 6/56 378/15 |
| 2008/0067873 A1 | | 3/2008 | Zhou et al. | |
| 2010/0270867 A1 | * | 10/2010 | Abe | H02J 7/025 307/104 |
| 2012/0326521 A1 | * | 12/2012 | Bauer | H02J 5/005 307/104 |

FOREIGN PATENT DOCUMENTS

JP 2002-065657 A 3/2002
WO 2008079870 A2 7/2008

OTHER PUBLICATIONS

Japanese Office Action cited in Japanese Application No. 2014-533270 dated Jun. 29, 2015, 3 pgs.
International Search Report cited in related application No. PCT/US11/054276 dated Jun. 12, 2012, pp. 15.

* cited by examiner

POWER DELIVERY TO A MOVING UNIT

BACKGROUND

The present application relates to the delivery of power to a moving and/or rotating unit. In particular, power may be delivered to two or more components utilizing different voltages concurrently via merely a single rotary transformer (e.g., comprised of a single set of primary and secondary windings) and/or other transference component that transfers power between a stationary unit and a rotating unit (e.g., or other unit configured to move relative to the stationary unit). Such power delivery systems and/or techniques find particular application in the context of computed tomography (CT) scanners, such as might be used in medical, security, and/or industrial applications, but may also be useful in other systems where two or more components of a moving unit that have different voltage requirements may be powered concurrently, for example.

Systems that comprise electronic components within a moving unit often require power to be provided to the moving unit via a power coupling apparatus. For example, in a CT scanner, power is supplied to an x-ray source and other electronics on a rotating gantry of the CT scanner from a stationary unit using a power coupling apparatus. One such power coupling apparatus is described in PCT Publication Number WO 2008/079870 to Adrian Delforge and assigned to Analogic Corporation.

With respect to CT scanners, the rotating gantry generally comprises numerous electronic components including, but not limited to, an x-ray tube, anode drive, tube heat exchanger, spine heater, and control electronics, for example. It will be appreciated that some of these electronic components, such the x-ray tube, may require as much as 100 kW or more of power while other electronic components that can operate concurrently with the x-ray tube may require much less power (e.g., 5 kW or less). Traditionally, two sets of power electronics have been utilized to provide the requisite power to the rotating gantry. A first set of power electronics (e.g., comprising a first inverter and a first set of windings) has been used to supply power to high voltage components, such as the x-ray source, and a second set of power electronics (e.g., comprising a second inverter and a second set of windings) has been used to supply power to other components that generally require a lower voltage.

While such techniques for providing power to the electronics of a CT system and/or other systems that require varying levels of power to be supplied to a moving unit have proven useful, there are several drawbacks to such techniques. For example, respective sets of power electronics may add weight (e.g., 50 pounds or more) to a moving unit and may consume space on the moving unit that is at a premium. As the desired RPM of rotating gantries in CT scanners continues to increase, the desire to decrease the weight of the rotating gantries has also increased. Additionally, it may be desirable to reduce the space consumed on a rotating gantry by power electronics to make room for other electronics that may further advance imaging capabilities of a CT scanner, for example.

SUMMARY

Aspects of the present application address the above matters, and others. According to one aspect, a method for concurrently delivering power to a high voltage component and a lower voltage component disposed on a reception unit configured for movement with respect to a transmission unit from which power is delivered to the reception unit is provided. The method comprises delivering a first voltage to the lower voltage component based at least in part upon a modulated amplitude of a modulated signal. The method also comprises concurrently delivering a second voltage to the high voltage component based at least in part upon a modulated frequency of the modulated signal, the first voltage different than the second voltage.

According to another aspect, a power delivery system is provided. The system comprises a rotary transformer comprising a primary winding and a secondary winding. The rotary transformer is configured to delivery power to a high voltage component and to a lower voltage component currently.

According to yet another aspect, a power delivery system is provided. The power delivery system comprises an inverter disposed on a transmission unit of the power delivery system and configured to modulate a frequency and an amplitude of a signal to generate an original modulated signal. The system also comprises a transference component configured to derive a modulated signal from the original modulated signal, the modulated signal comprising at least frequency and amplitude characteristics substantially consistent with the modulated frequency and the modulated amplitude of the original modulated signal. The system further comprises an auxiliary rectifier coupled to a first circuit electrically coupling the transference component to a lower voltage component, the auxiliary rectifier configured to adjust a voltage applied to the lower voltage component based at least in part upon the amplitude characteristic of the modulated signal. The system also comprises a filter component coupled to a second circuit electrically coupling the transference component to a high voltage component, the filter component comprising a frequency selective circuit configured to adjust a voltage applied to the high voltage component based at least in part upon the frequency characteristic of the modulated signal. The voltage applied to the high voltage component is different than the voltage applied to the lower voltage component.

Those of ordinary skill in the art will appreciate still other aspects of the present application upon reading and understanding the appended description.

FIGURES

The application is illustrated by way of example and not limitation in the figures of the accompanying drawings, in which like references indicate similar elements and in which.

DESCRIPTION

Figure 1:
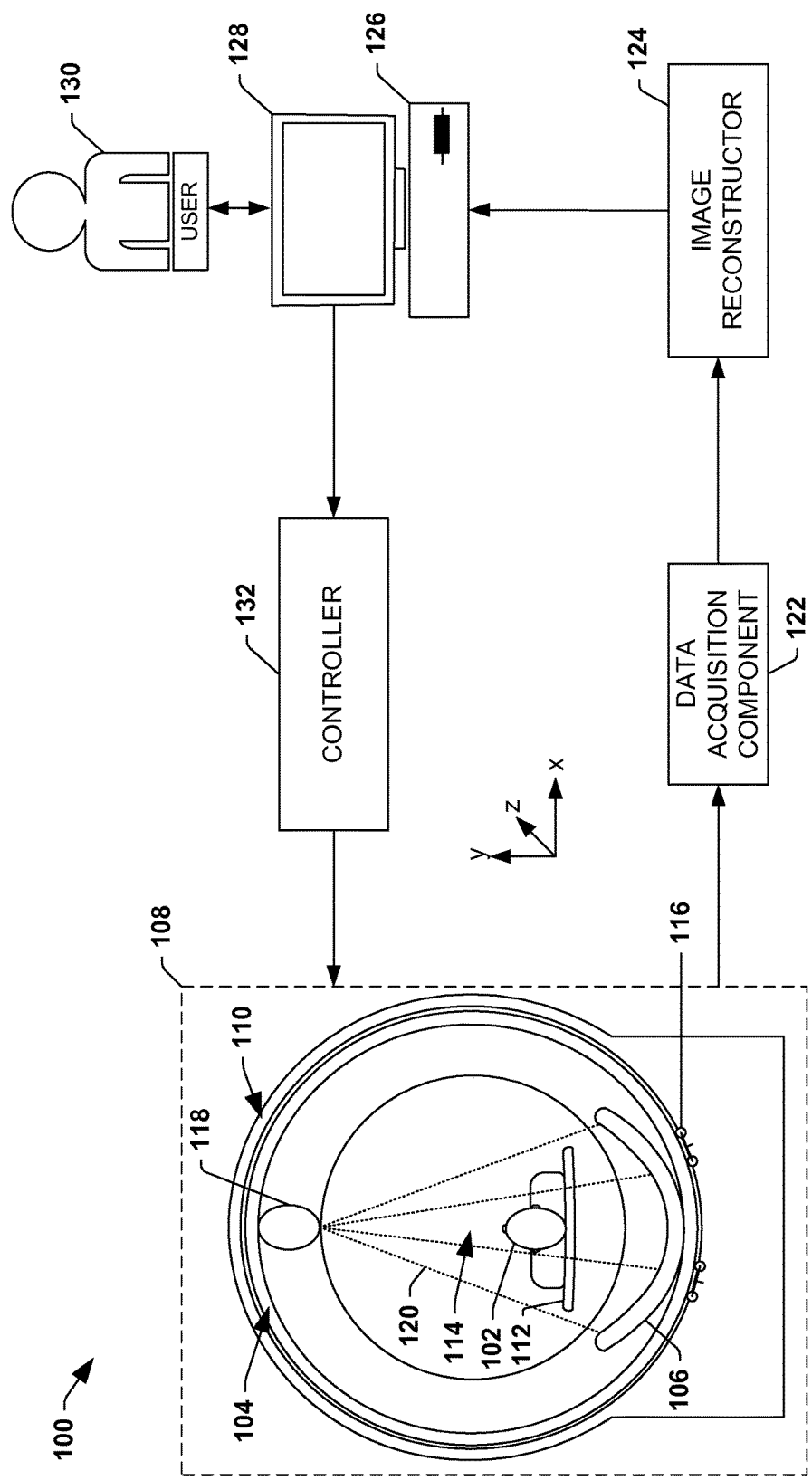
FIG. 1 is a schematic block diagram illustrating an example environment wherein a power delivery system such as described herein may be used.

The claimed subject matter is now described with reference to the drawings, wherein like reference numerals are generally used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are illustrated in block diagram form in order to facilitate describing the claimed subject matter.

The present disclosure relates to a power link, power coupling apparatus, etc. configured to transfer power between a transmission unit and a reception unit. Generally, at least one of the transmission unit and the reception unit are configured for motion, although both the transmission unit and the reception unit may be configured for motion. For example, in a CT modality, the transmission unit may be a stationary, support structure configured to support the reception unit, which may be configured to rotate relative to the transmission unit.

More particularly, the power link is configured to concurrently supply power to one or more high voltage components and one or more lower voltage components of the reception unit via a single transference component. For example, with respect to an imaging modality, the power link may be configured to concurrently supply power to an x-ray source (e.g., which may require 10 kW or more of power) and to auxiliary components, such as control electronics, spine heater, tube heat exchanger, and/or anode drive, etc. (e.g., which may require 5 kW or less of power) via a single rotary transformer (e.g., comprising a single primary winding and a single secondary winding).

The power supplied to the high voltage component(s) (e.g., x-ray source) and lower voltage component(s) (e.g., the auxiliary component(s)) is regulated by modulating at least two characteristics of a signal(s) (e.g., that are preferably orthogonal to one another) from which the power is derived. For example, in one embodiment, the amplitude and frequency of the signal(s) (e.g., which may also be referred to as waveforms, such that use of signal and/or the like herein, including in the claims, is intended to comprise waveform and/or the like as well) are modulated. That is, by modulating two or more characteristics of the signal (e.g., that are generally orthogonal with respect to one another), a first characteristic (e.g., amplitude) can be used to regulate the power supplied to lower voltage component(s) and a second characteristic (e.g., frequency) can be used to regulate the power supplied to the high voltage component(s). Stated differently, a first characteristic (e.g., amplitude) can be used to control an output voltage supplied to the lower voltage component(s) and a second characteristics (e.g., frequency) can be used as a control on a second circuit (e.g., through which power is delivered to the high voltage component(s)) and/or vice-versa.

It will be appreciated that the terms low voltage, lower voltage and the like are intended to be interpreted relative to the terms higher voltage, high voltage, and the like, and are not intended to be interpreted in a limiting manner such as necessarily specifying particular voltages and/or particular voltage ranges. For example, both the lower voltage component and the high voltage component may be configured to utilize voltages that have traditionally been considered low voltages (e.g., below 600 V), where the high voltage component may be configured to utilize a higher voltage than the lower voltage component. In yet another embodiment, the lower voltage component and the high voltage component may be configured to utilize what have traditionally been considered high voltages (e.g., 600 V or more), where the lower voltage component may be configured to utilize a lower voltage (e.g., but still a high voltage) than the high voltage component. In yet another embodiment, the lower voltage component may be configured to utilize a voltage that has traditionally been considered a low voltage (e.g., less than 600 V) and the high voltage component may be configured to utilize a voltage that has traditionally been considered a high voltage (e.g., equal to or greater than 600 V).

While the power link is described herein in some embodiments with respect to an imaging modality application, it will be appreciated that the instant disclosure, including the scope of the claims, is not intended to be limited to such applications. That is, to the extent practical, the techniques and/or systems described herein may be used with any applications where it may be desirable to transfer power between two or more units (e.g., and particularly in applications where at least two different levels of power are utilized by components comprised within a unit receiving the power transfer).

FIG. 1 is an illustration of an example environment 100 wherein a power link may be configured to transfer power between a transmission unit 110 (e.g., a stationary unit or stationary support structure) and a reception unit 104 (e.g., a rotating gantry) of an examination unit 108 that is configured to examine one or more objects 102. It will be appreciated that while reference is made to a computed tomography (CT) application, other imaging modality applications and/or applications unrelated to imaging modalities are contemplated. Moreover, the example environment 100 merely illustrates an example schematic and is not intended to be interpreted in a limiting manner, such as necessarily specifying the location, inclusion, and/or relative arrangement of the components described herein. For example, a data acquisition component 122 as illustrated in FIG. 1 may be part of the reception unit 104 of the examination unit 108, or more particularly may be part of a detector array 106, for example.

During an examination of the object(s) 102, the object(s) 102 can be placed on a support article 112, such as a bed or conveyor belt, for example, that is selectively positioned in an examination region 114 (e.g., a hollow bore in the reception unit 104), and the reception unit 104 can be rotated and/or supported about the object(s) 102 by a rotator 116, such as a motor, drive shaft, chain, roller truck, etc. During at least portions of the examination (e.g., such as when x-rays 120 are being emitted by an x-ray source 118), varying amounts of power may be supplied to various components comprised in the reception unit 104 via a rotary transformer (e.g., or other transference component) described in more detail below. For example, a substantially higher voltage may be supplied to the x-ray source 118 than to other components of the reception unit 104 (e.g., which may be referred to herein as auxiliary components) that are configured to receive a much lower voltage.

As illustrated, the reception unit 104 may surround a portion of the examination region 114 and may comprise, among other things, one or more x-ray sources 118 (e.g., an ionizing x-ray source) and a detector array 106 comprised of a plurality of pixels (e.g., also referred to as detectors) that is mounted on a substantially diametrically opposite side of the reception unit 104 relative to the x-rays source(s) 118. It will be appreciated that the reception unit 104 may also comprise other components (not shown) such as, but not limited to, control electronics, spine heater, tube heat exchanger, and/or an anode drive. Typically, the x-ray source(s) 118 is a high voltage component whereas most, if not all, of the other components comprised within the reception unit 104 (e.g. including the detector array 106) are lower voltage components (e.g., configured to operate at less than 600 V).

A typical examination unit 108 generally operates under two operating modes. During a first operating mode, which may be referred to as a preparation mode, power is generally supplied to the auxiliary component(s) (e.g., via a rotary transformer or other transference component) to prepare for an examination of the object. Once the auxiliary component(s) is prepared for an examination (e.g., an anode drive is rotating an anode of the x-ray source(s) 118, a heat exchanger is operational, etc.), the examination unit 108 transitions to a second operating mode, which may be referred to as a shoot mode, and x-rays may be emitted from the x-ray source(s) 118 to examine the object 102. It will be appreciated that during the shoot mode, power may be supplied to both the auxiliary component(s) and the x-ray source(s) (e.g., via a rotary transformer or other transference component). Thus, as will be described in more detail below, the transference component is configured to supply the auxiliary component(s) with low voltage power and to supply the x-ray source(s) 118 with high voltage power substantially concurrently.

During an examination of the object(s) 102, the x-ray source(s) 118 emits fan, cone, wedge, and/or other shaped x-ray configurations from a focal spot of the x-ray source 118 (e.g., a point within the x-ray source(s) 118 from which x-rays 120 emanate) and into the examination region 114. It will be appreciated that such x-rays 120 may be emitted substantially continuously and/or may be emitted intermittently (e.g., a short pulse of radiation is emitted followed by a resting period during which the x-ray source 118 is not activated).

As the emitted x-rays 120 traverse the object(s) 102, the x-rays 120 may be attenuated differently by different aspects of the object(s) 102. Because different aspects attenuate different percentages of the x-rays 120, an image(s) may be generated based upon the attenuation, or variations in the number of photons that are detected by the detector array 106. For example, more dense aspects of the object(s) 102, such as a bone or metal plate, may attenuate more of the x-rays 120 (e.g., causing fewer photons to strike the detector array 106) than less dense aspects, such as skin or clothing.

The detector array 106 can comprise a linear or two-dimensional array of pixels disposed as a single row or multiple rows in the shape of a circular, cylindrical, or spherical arc, for example, typically having a center of curvature at the focal spot of the radiation source(s) 118, for example. As x-rays 120 are emitted, the detector array 106 is configured to directly convert (e.g., using amorphous selenium and/or other direct conversion materials) and/or indirectly convert (e.g., using photodetectors and/or other indirect conversion materials) detected radiation into analog signals that can be transmitted from the detector array 106 to a data acquisition component 122 configured to periodically sample the analog signal(s) generated by respective pixels (e.g., respectively comprising one or more channels) and generate a digital output signal representative of one or more characteristics (e.g., density, z-effective, etc.) of a portion of the object 102 being examined during a measuring interval.

The collection of digital output signals generated by the data acquisition component 122 for a measuring interval and yielded from the analog signals respectively outputted by the pixels of the detector array 106 may be referred to as a "projection" or a "view". Moreover, an angular orientation of the reception unit 104 (e.g., and the corresponding angular orientations of the radiation source(s) 118 and the detector array 106) during generation of a projection may be referred to as the "projection angle."

As the reception unit 104 rotates around the object 102 under examination, the data acquisition component 122 generates a plurality of projections at a corresponding plurality of projection angles. It will be appreciated that the term "measured projection data" and/or the like is used herein to refer to this plurality of projections that are generated by the data acquisition component 122 and is indicative of the amount of radiation that the detector array 106 detected or measured.

The example environment 100 further comprises an image reconstructor 124 configured to receive the measured projection data output by the data acquisition component 122. The image reconstructor 124 is also configured to use analytical, iterative, and/or other image reconstruction algorithms and/or techniques to generate image data from the measured projection data (e.g., 2D filtered-backprojection, iterative reconstruction, etc.). Thus, the image reconstructor 124 may be configured to convert the measured projection data into volumetric data in image space. In this way, the data is converted from projection space to image space, a domain that may be more understandable by a user 130 viewing the image(s), for example.

The example environment 100 also includes a terminal 126, or workstation (e.g., a computer), configured to receive image(s) from the image reconstructor 124, which can be displayed on a monitor 128 to the user 130 (e.g., security personnel, medical personnel, etc.). In a CT modality, a displayed image(s) is typically a representation of one or more characteristics (e.g., density, z-effective, etc.) of a two-dimensional "slice" of the object (e.g., taken from the volumetric data) during the rotation of the reception unit 104 through the various projection angles. In this way, a user 130 can inspect the image(s) to identify areas of interest within the object(s) 102. The terminal 126 can also be configured to receive user input which can direct operations of the object examination apparatus 108 (e.g., a speed of rotation, an energy level of the radiation, etc.).

In the example environment 100, a controller 132 is operably coupled to the terminal 126. In one example, the controller 132 is configured to receive user input from the terminal 126 and generate instructions for the examination unit 108 indicative of operations to be performed.

Figure 2:
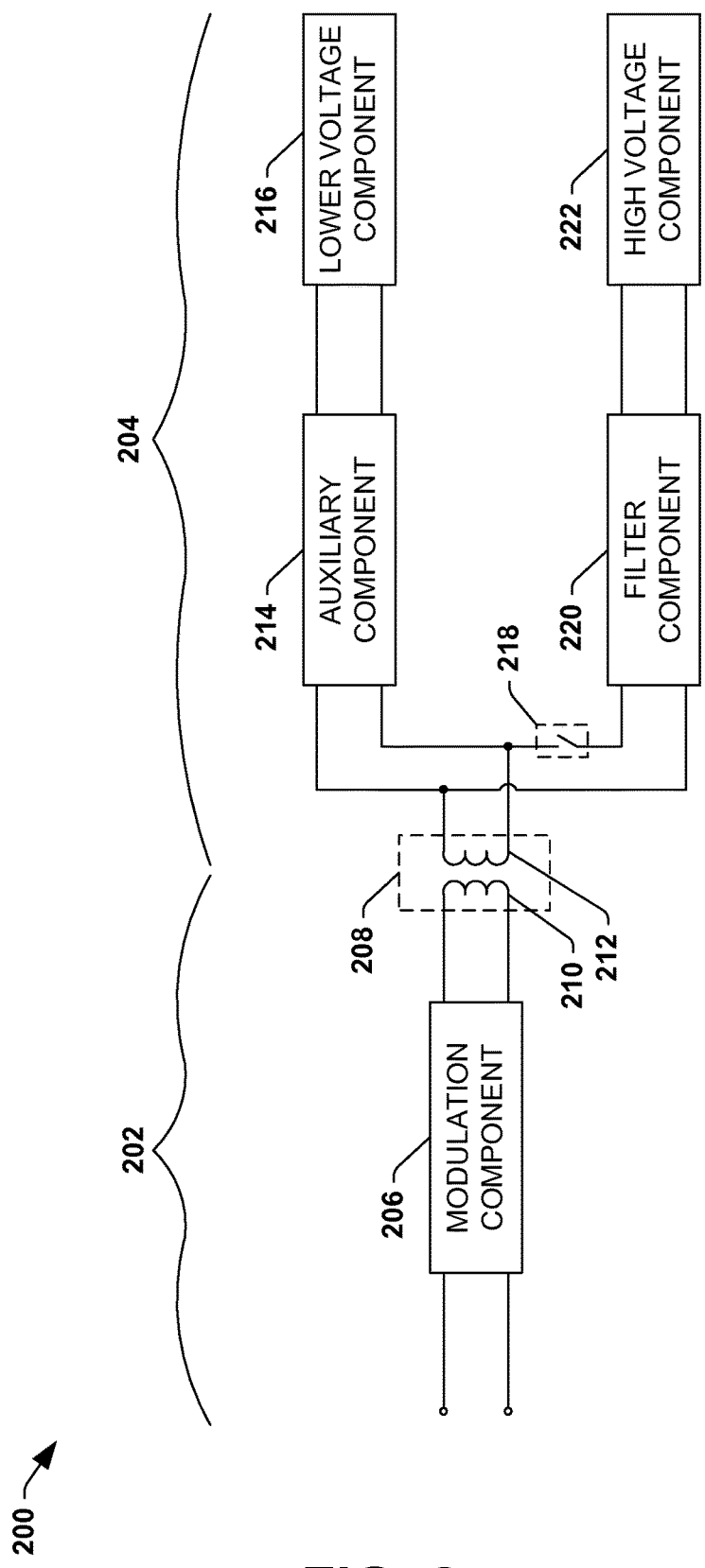
FIG. 2 illustrates an example power delivery system.

FIG. 2 illustrates an exemplary environment 200 of a power delivery system for transferring power between a transmission unit 202 (e.g., 110 in FIG. 1) and a reception unit 204 (e.g., 104 in FIG. 1). Typically, at least one of the transmission unit 202 and the reception unit 204 is configured for movement. For example, in one embodiment, the reception unit 204 may be configured for rotation relative to the transmission unit 202, which may be stationary, for example. As an example, in a CT application, the reception unit 204 may comprise a rotating gantry (e.g., comprising an x-ray source and detector array) configured to rotate with respect to the transmission unit 202, which may act as a support structure for the rotating gantry.

More particularly, the exemplary environment 200 illustrates an example power delivery system configured to, at times, concurrently delivery power to both a lower voltage component 216 and a high voltage component 222 via a transference component 208 (e.g., via a single rotary transformer).

The example power delivery system comprises a modulation component 206 (e.g., an inverter, high frequency inverter, high frequency resonant inverter, etc.) configured to receive an electrical, input signal (e.g., yielded from an electric generator) and to modulate at least two characteristics of the input signal (e.g., preferably orthogonal to one another) to generate an original modulated signal. For example, in one embodiment, the modulation component 206 is configured to modulate an amplitude and a frequency of the input signal using frequency and/or amplitude modulation techniques.

While the modulation component 206 may, at times, modulate two or more of the at least two characteristics of the input signal to yield an original modulated signal, it will be appreciated that at other times, one or none of the characteristics may be modulated. For example, where the modulated characteristics are the frequency and the amplitude of the input signal, the modulation component 206 may, at times, merely modulate one or none of the frequency and the amplitude and may, at other times, modulate both of the frequency and the amplitude. By way of example, the modulation component 306 may modulate amplitude when the lower voltage component 216 is drawing power (e.g., to regulate the voltage supplied to the lower voltage component 216) and may modulate frequency when the high voltage component 222 (e.g., an x-ray source) is drawing power (e.g., to regulate the voltage supplied to the high voltage component 222). Thus, during periods when the high voltage component 222 is not drawing power (e.g. during a prepare mode for the examination unit 108 in FIG. 1), merely the amplitude may be modulated, and during periods when both the high voltage component 222 and the lower voltage component 216 are drawing power (e.g. during a shoot mode for the examination unit 108 in FIG. 1), the modulation component 206 may be configured to concurrently modulate the amplitude and frequency of the input signal. At other times, the modulation component 206 may be configured to neither modulate the amplitude nor the frequency of the input signal. Regardless of what characteristic and/or characteristics of the input signal are modulated, the signal output by the modulation component 206 may be referred to herein as an original modulated signal.

The example environment 202 also comprises a transference component 208 configured to transfer power between the transmission unit 202 and the reception unit 204. Stated differently, the transference component 208 is configured to transfer the original modulated signal and/or characteristics thereof from the transmission unit 202 to the reception unit 204. It will be appreciated that for purposes of clarity, the signal may be referred to as the "original modulated signal" when the signal is within the transmission unit 202 and may be referred to as a "modulated signal" when the signal is within the reception unit 204.

By way of example, in the illustrated embodiment, the transference component 208 comprises a rotary transformer comprising a primary winding 210 (e.g., disposed on the transmission unit 202) and a secondary winding 212 (e.g., disposed on the reception unit 204). As will be appreciated, the rotary transformer is configured to generate a modulated signal (e.g., induce a current) on the secondary winding 212 based at least in part upon the original modulated signal, which is passed through the primary winding 210. Stated differently, the original modulated signal is passed through the primary winding 210 to induce the modulated signal in the secondary winding 212.

While the secondary winding 212 may be configured to increase (e.g., step up) or decrease (e.g., step down) a voltage of the modulated signal relative to a voltage of the original modulated signal (e.g., and/or alter other characteristics of the modulated signal relative to similar characteristics of the original modulated signal), in one embodiment, the secondary winding 212 is configured to merely generate a modulated signal that substantially matches the original modulated signal. Thus, amplitude, frequency, and/or other characteristics of the modulated signal output by the secondary winding 212 may substantially match amplitude, frequency, and/or other characteristics of the original modulated signal, for example.

In another embodiment of the power delivery system, the transference component 208 may comprise a slip ring, and the original modulated signal may be transferred to the reception unit 204 via a brush and ring assembly. Thus, the original modulated signal may be transferred to the reception unit 204 via the slip ring (e.g., as opposed to a modulated signal being generated on the reception unit 204 based upon the original modulated signal, for example). Where the original modulated signal may be transferred to the reception unit 204 via the slip ring, however, once on the reception unit 204 the original modulated signal may be regarded as the modulated signal.

Regardless of embodiment (e.g., rotary transformer, slip ring, etc.), the modulated signal is channeled to at least two different circuits of the reception unit 204. A first circuit is configured to deliver power from the transference component 208 to the lower voltage component 216, and typically comprises, among other things, an auxiliary component 214 and the lower voltage component 216. The second circuit is configured to deliver power from the transference component 208 to the high voltage component 222, and typically comprises, among other things, a switch 218, a filter component 220, and a high voltage component 222.

The auxiliary component 214 is configured to adjust the voltage that is applied to the lower voltage component 216 based at least in part upon a first modulated characteristic of the modulated signal. For example, in one embodiment, the auxiliary component 214 is configured to adjust the voltage applied to the lower voltage component 216 based at least in part upon a modulated amplitude of the modulated signal. Thus, the modulated amplitude of the modulated signal may be utilized by the auxiliary component 214 to regulate an output voltage (e.g., on the secondary winding 212 of the rotary transformer if a rotary transformer is used) that is applied to the lower voltage component 216 using regulation techniques. Typically, such techniques regulate the voltage applied to the lower voltage component 216 substantially independent of a second modulated characteristic (e.g., such as a modulated frequency) of the modulated signal. Thus, where amplitude and frequency are modulated by the modulation component 206, the modulated frequency may have little to no effect on a voltage that is applied to the lower voltage component 216.

Moreover, in one embodiment, the lower voltage component 216 may be configured to receive a direct current signal, and thus the auxiliary component 214 may be further configured to convert the modulated signal from an AC signal to a DC signal (e.g., if the modulated signal yielded from the transference component 208 is an AC signal). For example, in one embodiment, the auxiliary component 214 may comprise a rectifier configured to convert the modulated signal from AC to DC.

The example environment 200 of the first circuit further comprises the lower voltage component 216 configured to receive a signal output by the auxiliary component 214 (e.g., comprising characteristics desired and/or required by the lower voltage component 216) and to extract power from the signal output by the auxiliary component 214. By way of example and not limitation, in a CT application, the lower voltage component 216 may comprise, among other things, control electronics, a spine heater, a tube heat exchanger, an anode driver, and/or a detector array.

The example environment 200 also comprises a second circuit through which power is delivered from the transference component 208 to the high voltage component 222. Generally speaking, the second circuit comprises the switch 218, the filter component 220, and the high voltage component 222.

The switch 218 is configured to electrically uncouple (e.g., interrupt the flow of current between) the transference component 208 and the high voltage component 222. In this way, current can be interrupted when no power is intended to be supplied to the high voltage component 222. By way of example, in a CT application, the switch 218 can be configured to control the emission of x-rays from the high voltage component 222 (e.g., an x-ray source). When the switch 218 is open (e.g., when the examination unit 108 in FIG. 1 is in prepare mode), no power may be supplied to the high voltage component 222 and no x-rays may be emitted. When the switch 218 is closed (e.g., when the examination unit 108 in FIG. 1 is in shoot mode), power may be supplied to the high voltage component 222 and x-rays may be emitted.

It will be appreciated that the switch 218 can be controlled by control electronics (e.g., not shown) within the reception unit 204 and/or via other control mechanisms. For example, in one embodiment, instructions can be transmitted wirelessly from the transmission unit 202 to a control circuit of the reception unit 204 that is configured to control the switch 218.

The filter component 220 of the example environment 200 is configured to control an output voltage supplied to the high voltage component 222 based upon a second characteristic that is modulated by the modulation component 206. Stated differently, the filter component 220 is configured to adjust a voltage applied to the high voltage component 222 based at least in part upon a modulated characteristic of the modulated signal that is different than the characteristic used by the auxiliary component 214 to adjust the voltage applied to the lower voltage component 216.

By way of example, where the modulation component 206 is configured to modulate the frequency of the signal, the filter component 220 may comprise a frequency selective circuit, such as a highpass filter, bandpass filter, and/or bandstop filter, for example, that is configured to filter out portions of the modulated signal that are not within a specified frequency range from other portions of the modulated signal (e.g., that do not comprise a frequency within the specified frequency range). In one example, the filter component 220 comprises an LC circuit comprised of an inductor and a capacitor configured to filter out frequencies of the modulated signal outside of a specified range; however, other frequency selective circuits are contemplated herein. In this way, the output voltage of the filter component 220 may be greater than the input voltage (e.g., causing the voltage applied to the high voltage component 222 to be greater than the voltage applied to the lower voltage component 216), for example.

The example environment 200 further comprises the high voltage component 222 configured to receive a signal output by the filter component 220 and to extract power from the signal. By way of example and not limitation, in a CT application, the high voltage component 222 may comprise, among other things, an anode of an x-ray source (e.g., 118 in FIG. 1).

It will be appreciated that example environment 200 of FIG. 2 merely illustrates example components of a power delivery system, and is not intended to be viewed in a limiting manner necessarily specifying all of the components of the power delivery system. For example, in one embodiment, the high voltage component 222 may desire and/or may be required to receive a DC signal. Therefore, if the filter component 220 and/or the transference component 208 output an AC signal, the second circuit may further comprise a high voltage rectifier (e.g., as will be further described in FIG. 3), configured to rectify the signal output by the filter component 220 to generate a high voltage DC signal that may be received by the high voltage component 222, for example.

Figure 3:
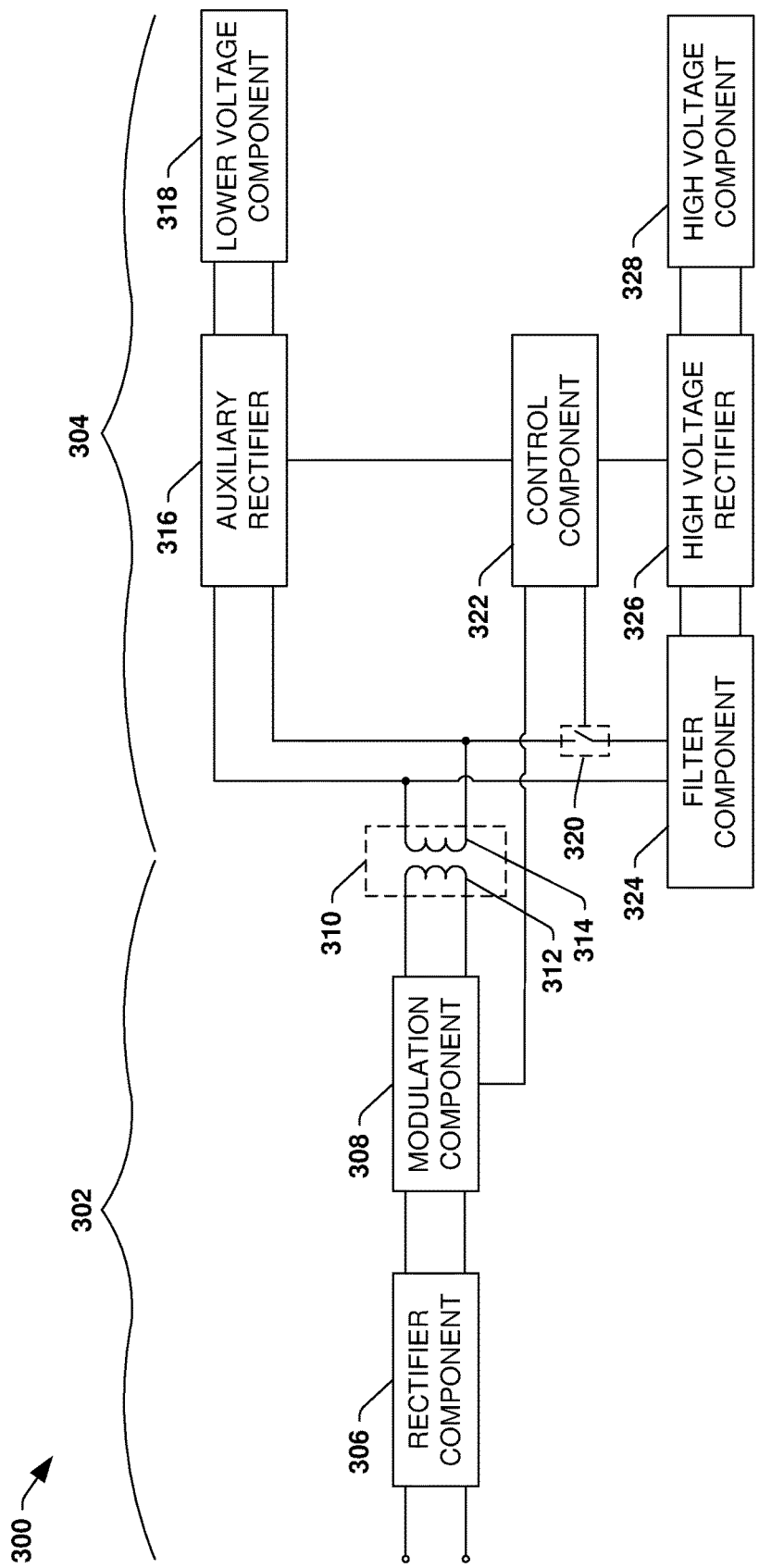
FIG. 3 illustrates an example power delivery system.

FIG. 3 illustrates yet another embodiment of an exemplary environment of a power delivery system configured to transfer power between a transmission unit 302 (e.g., 110 in FIG. 1) and a reception unit 304 (e.g., 104 in FIG. 1). Typically, at least one of the transmission unit 302 and the reception unit 304 is configured for movement. For example, in one embodiment, the reception unit 304 may be configured for rotation relative to the transmission unit 302, which may be stationary, for example. As an example, in a CT application, the reception unit 304 may comprise a rotating gantry (e.g., comprising an x-ray source and detector array) configured to rotate with respect to the transmission unit 302, which may act as a support structure for the rotating gantry.

More particularly, the exemplary environment 300 illustrates an example power delivery system configured to, at times, concurrently delivery power to both a lower voltage component 318 (e.g., 216 in FIG. 2) and a high voltage component 328 (e.g., 222 in FIG. 2) via a transference component 310 (e.g., 208 in FIG. 2) (e.g., via a single rotary transformer).

The example environment 300 of the power delivery system comprises a rectifier component 306 configured to rectify an input electrical signal (e.g., yielded from an electric generator). That is, the rectifier component 306 may be configured to convert an input signal comprising an alternating current (AC) to a signal comprising a direct current (DC). Moreover, the rectifier component 306 may be configured to alter other characteristics of the input signal to improve the quality of the signal and/or to make adjustments to the signal. For example, in one embodiment, the rectifier component 306 may adjust or correct a phase of the input signal.

The example environment further comprises a modulation component 308 (e.g., 206 in FIG. 2) configured to receive the signal output by the rectifier component 306. The modulation component 308 is also configured to invert the received signal (e.g., converting the signal from DC to AC) and to modulate at least two characteristics of the inverted signal (e.g., preferably orthogonal to one another) to generate an original modulated signal comprising an alternating current. For example, in one embodiment, the modulation component 308 is configured to modulate an amplitude and a frequency of the received signal using frequency and/or amplitude modulation techniques.

By way of example, the modulation component 308 may comprise an inverter, such as high frequency inverter, high frequency resonant inverter, and/or a high frequency series resonant invertor, for example, configured to convert the received DC signal into an AC signal having a frequency or frequency range that is greater than the original AC signal that was received by the rectifier component 306. For example, in one embodiment, the modulation component may increase the frequency range by a multiplication factor of one thousand relative to the frequency range of the signal input into the rectifier component 306 (e.g., changing the frequency range of the signal from 50-60 Hz to 50-60 kHz).

It will be appreciated that increasing the frequency range may improve the ease with which power can be transferred via a rotary transformer (e.g., if the transference component 310 comprises a rotary transformer). Stated differently, a higher frequency range, generally promotes a reduction in the size of associated magnetic components and therefore a reduction in the size and/or weight of the rotary transformer. However, in some embodiments, the size and/or weight of the rotary transformer may be immaterial (e.g., if a rotary transformer is not used (e.g., slip ring is used) to transfer power between the transmission unit 302 and the reception unit 304), and thus, the modulation component 308 may not be configured to increase the frequency range of the signal and/or may be configured to increase the frequency range of the signal by a smaller multiplication factor (e.g., because a high frequency is not needed).

As described above, the modulation component 308 is configured to modulate at least two characteristics of the received signal to yield an original modulated signal. While, at times, two or more of the at least two characteristics may be modulated concurrently, it will be appreciated that at other times, one or none of the characteristics may be modulated. For example, where the modulated characteristics are frequency and amplitude, the modulation component 308 may, at times, merely modulate one or none of the frequency and the amplitude and may, at other times, modulate both of the frequency and the amplitude. By way of example, the modulation component 308 may modulate amplitude when the lower voltage component 318 is drawing power (e.g., to regulate the voltage supplied to the lower voltage component 318) and may modulate frequency when the high voltage component 328 (e.g., an x-ray source) is drawing power (e.g., to regulate the voltage supplied to the high voltage component 328). Thus, during periods when the high voltage component 328 is not drawing power (e.g. during a prepare mode for the examination unit 108 in FIG. 1), merely the amplitude may be modulated, and during periods when both the high voltage component 328 and the lower voltage component 318 are drawing power (e.g. during a shoot mode for the examination unit 108 in FIG. 1), the modulation component 308 may be configured to concurrently modulate the amplitude and frequency of the received signal. At other times, the modulation component 308 may be configured to neither modulate the amplitude nor the frequency of the received signal. Regardless of what characteristic and/or characteristics of the received signal are modulated, the signal output by the modulation component 308 may be referred to herein as an original modulated signal.

The example environment 300 also comprises a transference component 310 (e.g., 208 in FIG. 2) configured to transfer power between the transmission unit 302 and the reception unit 304. Stated differently, the transference component 310 is configured to transfer the original modulated signal and/or characteristics thereof from the transmission unit 302 to the reception unit 304.

By way of example, in the illustrated embodiment, the transference component 310 comprises a rotary transformer comprising a primary winding 312 (e.g., disposed on the transmission unit 302) and a secondary winding 314 (e.g., disposed on the reception unit 304). As will be appreciated, the rotary transformer is configured to generate a modulated signal (e.g., induce a current) on the secondary winding 314 based at least in part upon the original modulated signal, which is passed through the primary winding 312. Stated differently, the original modulated signal is passed through the primary winding 312 to induce the modulated signal in the secondary winding 314.

While the secondary winding 314 may be configured to increase (e.g., step up) or decrease (e.g., step down) a voltage of the modulated signal relative to a voltage of the original modulated signal (e.g., and/or alter other characteristics of the modulated signal relative to similar characteristics of the original modulated signal), in one embodiment, the secondary winding 314 is configured to merely generate a modulated signal that substantially matches the original modulated signal. Thus, amplitude, frequency, and/or other characteristics of the modulated signal output by the secondary winding 314 may substantially match amplitude, frequency, and/or other characteristics, respectively, of the original modulated signal, for example.

In another embodiment of the power delivery system, the transference component 310 may comprise a slip ring, and the original modulated signal may be transferred to the reception unit 304 via a brush and ring assembly. Thus, the original modulated signal may be transferred to the reception unit 304 via the slip ring (e.g., as opposed to a modulated signal being generated on the reception unit 304 based upon the original modulated signal, for example). It will be appreciated that for purposes of consistency, clarity, etc., the term modulated signal may thus be used to refer to either a new signal that is generated on the reception unit 304 (e.g., via a secondary winding 314) and/or the original modulated signal after it has been transferred to the reception unit 304 (e.g., via slip ring).

Regardless of embodiment (e.g., rotary transformer, slip ring, etc.), the modulated signal is channeled to at least two different circuits of the reception unit 304. A first circuit is configured to deliver power from the transference component 310 to the lower voltage component 318 and typically comprises, among other things, an auxiliary rectifier 316 (e.g., 214 in FIG. 2) and the lower voltage component 318. The second circuit is configured to deliver power from the transference component 310 to the high voltage component 328, and typically comprises, among other things, a switch 320 (e.g., 218 in FIG. 2), a filter component 324 (e.g., 220 in FIG. 2), a high voltage rectifier 326, and the high voltage component 328.

The auxiliary rectifier 316 is configured to rectify the modulated signal (e.g., which is an AC signal because the original modulated signal was an AC signal) and adjust the voltage that is applied to the lower voltage component 318 based at least in part upon a first modulated characteristic of the modulated signal. For example, in one embodiment, the auxiliary rectifier 316 is configured to adjust the voltage applied to the lower voltage component 318 based at least in part upon a modulated amplitude of the modulated signal. Thus, the modulated amplitude of the modulated signal may be utilized by the auxiliary rectify 316 to regulate an output voltage (e.g., on the secondary winding 314 of the rotary transformer if a rotary transformer is used) that is applied to the lower voltage component 318 using regulation techniques. In one embodiment, such techniques regulate the voltage applied to the lower voltage component 318 substantially independent of one or more other characteristics of the modulated signal (e.g., corresponding to other characteristics of the original modulated signal that were modulated by the modulation component 308). For example, where the modulated signal comprises a modulated amplitude and a modulated frequency, the auxiliary rectifier 316 may be configured to adjust an output voltage applied to the lower voltage component 318 substantially independent of the frequency modulation. Thus, the modulated frequency may have little to no effect on a voltage that is applied to the lower voltage component 318.

The example environment 300 of the first circuit further comprises a lower voltage component 318 configured to receive a signal output by the auxiliary rectifier 316 (e.g., comprising characteristics desired by the lower voltage component 318) and to extract power from the signal output by the auxiliary rectifier 316. By way of example and not limitation, in a CT application, the lower voltage component 216 may comprise, among other things, control electronics, a spine heater, a tube heat exchanger, an anode driver, and/or a detector array.

The example environment 200 also comprises a second circuit through which power is delivered from the transference component 310 to the high voltage component 328. Generally speaking, the second circuit comprises the switch 320, the filter component 324, the high voltage rectifier 326, and the high voltage component 328.

The switch 320 is configured to electrically uncouple (e.g., interrupt the flow of current between) the transference component 310 and the high voltage component 328. In this way, current can be interrupted when no power is intended to be supplied to the high voltage component 328. By way of example, in a CT application, the switch 320 can be configured to control the emission of x-rays from the high voltage component 328 (e.g., an x-ray source). When the switch 320 is open (e.g., when the examination unit 108 in FIG. 1 is in prepare mode), no power may be supplied to the high voltage component 328 and no x-rays may be emitted. When the switch 320 is closed (e.g., when the examination unit 108 in FIG. 1 is in shoot mode), power may be supplied to the high voltage component 328 and x-rays may be emitted.

It will be appreciated that the switch 320 can be controlled by a control component 322 that is configured to receive data and/or other information from an outside source and/or from the modulation component 308. For example, in one embodiment, instructions can be transmitted wirelessly from the transmission unit 302 to a control component 322 of the reception unit 304 that is configured to control the switch 320. Moreover, in one embodiment, the control component 322 may be configured to monitor the modulated signal that is transmitted to various components of the reception unit 304 and/or to provide instructions for adjusting one or more characteristics of the modulated signal. For example, in one embodiment, the control component 322 may be configured to receive data and/or signals from the auxiliary rectifier 316 and/or the high voltage rectifier 326 indicative of the signals being provided to the lower voltage component 318 and/or the high voltage component 328, respectively. The control component 322 may proceed to analyze the received data and/or signals and issue instructions and/or requests that adjustments be made to the signals supplied to the lower voltage component 318 and/or the high voltage component 328. In one example, the control component 322 may issue an instruction requesting that the modulation component 308 modify the way at least one characteristic is modulated to adjust the signals supplied to the lower voltage component 318 and/or the high voltage component 328.

The filter component 324 of the example environment 300 is configured to control an output voltage supplied to the high voltage component 328 based upon a second characteristic that is modulated by the modulation component 308. Stated differently, the filter component 324 is configured to adjust a voltage applied to the high voltage component 328 based at least in part upon a modulated characteristic of the modulated signal that is different than the characteristic used by the auxiliary rectifier 316 to adjust the voltage applied to the lower voltage component 318.

By way of example, where the modulation component 308 is configured to modulate the frequency of the signal, the filter component 324 may comprise a frequency selective circuit, such as a highpass filter, bandpass filter, and/or bandstop filter, for example, that is configured to filter out portions of the modulated signal that are not within a specified frequency range from other portions of the modulated signal (e.g., that do not comprise a frequency within the specified frequency range). In one example, the filter component 324 comprises an LC circuit comprised of an inductor and a capacitor configured to filter out frequencies of the modulated signal outside of a specified range; however, other frequency selective circuits are contemplated herein. In this way, the output voltage of the filter component 324 may be greater than the input voltage (e.g., causing the voltage applied to the high voltage component 328 to be greater than the voltage applied to the lower voltage component 318), for example.

The example environment also comprises a high voltage rectifier 326 configured to rectify the portion of the modulated signal that passes through the filter component 324 (e.g., which is an AC signal because the original modulated signal was an AC signal). In this way, the signal is converted from an AC signal to a DC signal that may be desired and/or required by the high voltage component 328.

The example environment 300 further comprises the high voltage component 328 configured to receive a signal output by the high voltage rectifier 326 and to extract power from the signal. By way of example and not limitation, in a CT application, the high voltage component 328 may comprise, among other things, an anode of an x-ray source (e.g., 118 in FIG. 1).

It will be appreciated that example environment 300 of FIG. 3 merely illustrates example components of a power delivery system, and is not intended to be viewed in a limiting manner as necessarily specifying and/or illustrating all of the components of the power delivery system. Moreover, at least some of the components described herein may be optional. For example, the power delivery system may not comprise the high voltage rectifier 326 if the high voltage component 328 is configured to receive an AC signal and/or may not comprise the rectifier component 306 if the signal input into the power delivery system is a DC signal, for example.

Figure 4:
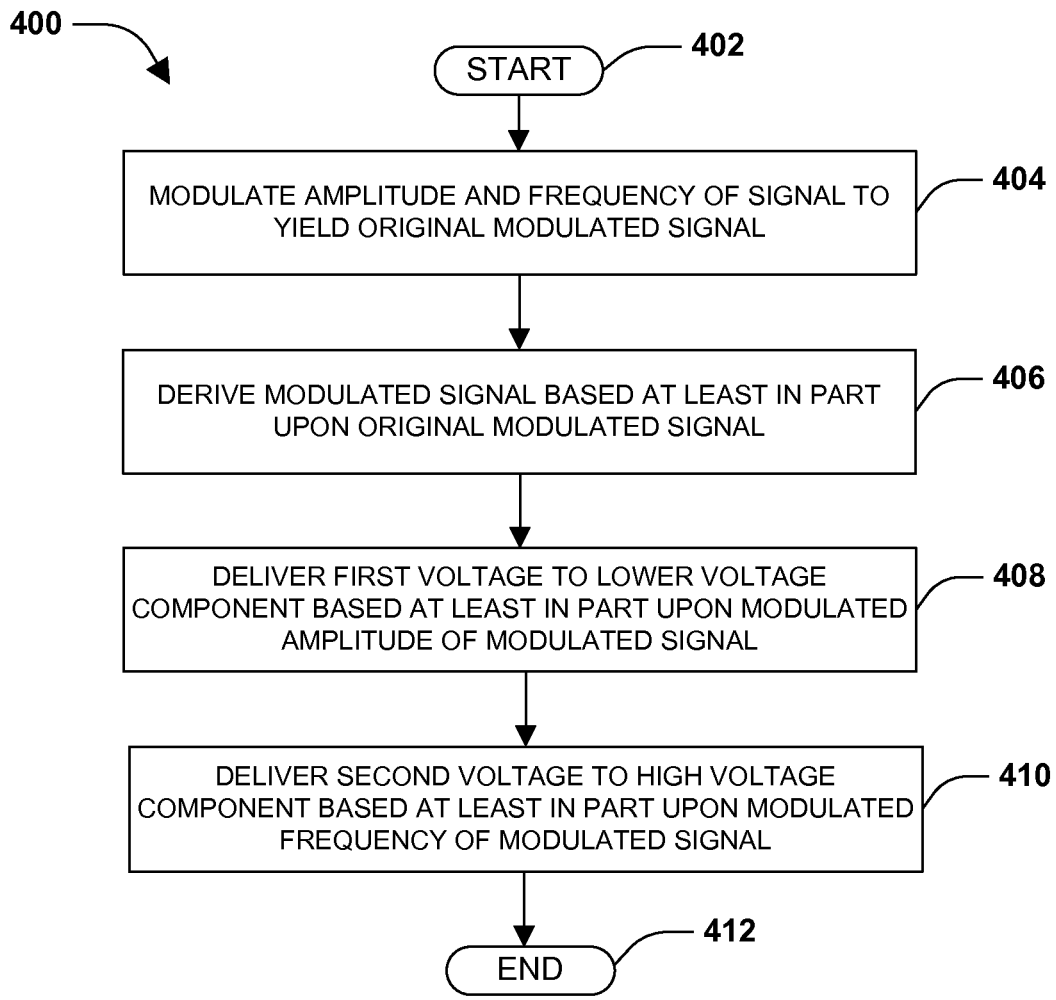
FIG. 4 is a flow diagram illustrating an example method for concurrently delivering power to a high voltage component and a lower voltage component disposed on a reception unit configured for movement with respect to a transmission unit from which the power is delivered to the reception unit.

FIG. 4 illustrates an example method 400 for concurrently delivering power to a high voltage component (e.g., 328 in FIG. 3) and a lower voltage component (e.g., 318 in FIG. 3) disposed on a reception unit. Generally, the reception unit is configured for motion relative to a transmission unit (e.g., from which power is delivered to the reception unit and/or component(s) thereof), although both the transmission unit and the reception unit may be configured for motion. For example, in a CT modality, the transmission unit may be a stationary, support structure configured to support the reception unit, which may be configured to rotate relative to the transmission unit.

The power supplied to the high voltage component and lower voltage component may be regulated by modulating at least two characteristics of a signal(s) (e.g., that are preferably orthogonal to one another) from which the power is derived. For example, in one embodiment, the amplitude and frequency of the signal(s) are modulated. That is, by modulating two or more characteristics of the signal(s) (e.g., that are generally orthogonal with respect to one another), a first characteristic (e.g., amplitude) can be used to regulate the voltage (e.g., and therefore power) supplied to the lower voltage component and a second characteristic (e.g., frequency) can be used to regulate the voltage supplied to the high voltage component.

The method 400 begins at 402 and at least two characteristics of an input, electric signal are modulated at 404 to yield an original modulated signal. In one embodiment, it is preferred that at least two of the characteristics that are modulated at 404 be orthogonal characteristics. For example, the frequency and amplitude of an electric signal may be modulated since frequency and amplitude are orthogonal characteristics of the signal.

It will be appreciated that other properties of the input signal may be altered prior to and/or after the modulation has occurred. For example, in one embodiment, the input signal may be an alternating current (AC) signal and the input signal may be rectified to yield a direct current (DC) signal which can then be utilized to increase the frequency of the signal relative to the input signal. As an example, an inverter, such as high frequency inverter, resonant inverter, and/or high frequency resonant inverter, for example, can be configured to convert the direct current signal into an AC signal having an increased frequency range relative to the frequency range of the input signal. Thus, besides modulating at least two characteristics of the input signal, one or more other properties of the signal can be adjusted to yield the original modulated signal.

At 406 in the example method, a modulated signal is derived based at least in part upon the original modulated signal. For example, in one embodiment, a rotary transformer is utilized to transfer power from the transmission unit to the reception unit. As described with respect to FIGS. 2-3, the rotary transformer can comprise a primary winding disposed on the transmission unit and a secondary winding disposed on the reception unit. The original modulated signal can be passed through the primary winding to derive (e.g., induce) a signal on the secondary winding that can be utilized by the lower voltage component and the high voltage component for power. In another embodiment, the original modulated signal can be transmitted to the transmission component via a slip ring assembly to derive the modulated signal (e.g., which may be the same signal as the original modulated signal). Thus, the terms "original modulated signal" may be used herein in a broad sense to describe a signal created on the transmission unit for example and the terms "modulated signal" may be used herein in a broad sense to describe a signal derived at and/or transferred to the reception unit. It will be appreciated that depending upon how power is transferred to the reception unit, the modulated signal may be the same signal as the original modulated signal and/or may be a new signal generated from the original modulated signal. That is, the term "derive" and/or the like can be interpreted to simply mean obtaining the original modulated signal from the transmission unit, for example.

Moreover, where the power is transferred from the transmission unit to the reception unit via a rotary transformer, it will be appreciated that characteristics of the modulated signal may be different than characteristics of the original modulated signal and/or the modulated signal may have the same characteristics as the original modulated signal. For example, the rotary transformer may be configured step-up or step-down a voltage relative to the original modulated signal. However, the at least two characteristics of the input signal that were modulated to yield the original modulated signal are generally (e.g., preferably) characteristics of the modulated signal, and in one embodiment, substantially all of the characteristics of the modulated signal are the same as corresponding characteristics of the original modulated signal. As an example, where the amplitude and the frequency of the input signal were modulated to yield the original modulated signal, the modulated signal generally comprises, at the very least, amplitude and frequency characteristics that substantially match the modulated amplitude and frequency characteristics of the original modulated signal.

At 408 in the example method 400, a first voltage is delivered to the lower voltage component based at least in part upon a first modulated characteristic of the modulated signal. For example, the first voltage may be adjusted and/or regulated (e.g., by an auxiliary rectifier) based upon a modulated amplitude of the modulated signal. Typically, adjustments and/or regulations of the first voltage that is delivered to the lower voltage component are not a function of at least one of the other modulated characteristics of the modulated signal. For example, where the modulated signal comprises a modulated amplitude and a modulated frequency, the adjustments and/or regulation of the first voltage may not be a function of modulated frequency if such adjustments and/or regulations are a function of the modulated amplitude.

At 410 in the example method 400, a second voltage is delivered to the high voltage component based at least in part upon a second modulated characteristic of the modulated signal. For example, the second voltage may be adjusted and/or regulated (e.g., by a frequency selective circuit) based upon a modulated frequency of the modulated signal. In this way, the second voltage is adjusted and/or regulated by a different modulated characteristic than the first voltage, such that the first and second voltages can be adjusted and/or regulated using the same modulated signal. That is, stated differently, the modulated signal can be used to regulate voltages applied to the lower voltage component and the high voltage component.

At 412, the example method 400 ends.

By way of example and not limitation, the example method 400 may find applicability to a power delivery system of a computed tomography image modality and/or other image modalities that comprise one or more moving portions. For example, an input electric signal may be supplied to transmission unit (e.g., stationary side) of the computed tomography image modality. If the input electric signal is an AC signal, the signal may be rectified and/or other characteristics of the signal may be adjusted (e.g., a phase may be corrected) by a front-end rectifier, for example. The signal may be then transmitted to an inverter, for example, configured to invert the signal into an AC signal that has a different frequency and/or frequency range than the input signal supplied to the computed tomography image modality. Moreover, one or more characteristics (e.g., which may also be referred to herein as properties) of the signal may be modulated to yield an original modulated signal (e.g., as described in act 404 of the example method 400). By way of example, in one embodiment, at least the amplitude and the frequency of the signal may be modulated to yield the original modulated signal.

The original modulated signal may then be utilized to derive a modulated signal on the reception unit (e.g., rotating gantry) of the computed tomography image modality (e.g., as described in act 406 of the example method 400). In this way, power may be transferred from the transmission unit to the reception unit. It will be appreciated that there are numerous ways to transfer power between a transmission unit (e.g., which may be stationary) and a reception unit (e.g., which may be moving and/or rotating). For example, in one embodiment, a rotary transformer comprising a primary winding and a secondary winding may be utilized to transfer the power. In such an embodiment, the original modulated signal may be passed through the primary winding to generate a modulated signal in the secondary winding. In this way, a new signal is generated (e.g., derived) from the original modulated signal. As described above, while one or more characteristics of the original modulated signal may differ from the one or more characteristics of the modulated signal (e.g., depending upon whether the primary and secondary windings have a same or different number of turns), typically at least the modulated characteristics that are used to adjust/regulate voltages applied to the lower voltage component and the high voltage component are substantially the same in both the original modulated signal and the modulated signal.

In another embodiment, a slip ring assembly may be utilized to transfer the power and the original modulated signal may be transmitted to the reception unit (e.g., such that no new signal is generated). However, for purposes of consistency, the original modulated signal may be renamed herein as a modulated signal when it is transferred from the transmission unit to the reception unit.

The modulated signal may be used to adjust/regulate voltages that are applied to both the lower voltage component (e.g., control electronics, spine heater, tube heat exchange, anode drive, detector array, etc.) and the high voltage component (e.g., an anode of the x-ray source). For example, a first component (e.g., an auxiliary component, such as an auxiliary rectifier) may be configured to adjust/regulate a voltage that is applied to lower voltage component based upon a first modulated characteristic of the modulated signal, such as an amplitude characteristic of the modulated signal, for example (e.g., as described in act 408 of the example method 400). A second component (e.g., a frequency selective circuit, such as an LC circuit) may be configured to adjust/regulate a voltage that is applied to the high voltage component based upon a second modulated characteristic of the modulated signal, such as an amplitude characteristic of the modulated signal, for example (e.g., described in act 410 of the example method 400). Generally, the first component is configured to operate substantially independent of the second modulated characteristic such that a voltage applied to the lower voltage component is not adjusted/regulated based upon the second modulated characteristic, for example.

The words "example" and/or "exemplary" are used herein to mean serving as an example, instance, or illustration. Any aspect, design, etc. described herein as "example" and/or "exemplary" is not necessarily to be construed as advantageous over other aspects, designs, etc. Rather, use of these terms is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form. Also, at least one of A and B or the like generally means A or B or both A and B.

Although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, items, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. Similarly, illustrated ordering(s) of acts is not meant to be limiting, such that different orderings comprising the same of different (e.g., numbers) of acts are intended to fall within the scope of the instant disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A power delivery system, comprising:
a rotary transformer comprising a primary winding and a secondary winding, wherein:
the rotary transformer is configured to deliver first power to a high voltage component and second power to a lower voltage component concurrently, and
the secondary winding is configured to produce a modulated signal comprising at least a modulated amplitude and a modulated frequency; and
an auxiliary component disposed on a first circuit through which the second power is delivered via the modulated signal from the secondary winding to the lower voltage component, wherein:
the auxiliary component comprises a rectifier, and
the auxiliary component is configured to adjust a first voltage applied to the lower voltage component based at least in part upon the modulated amplitude of the modulated signal.

2. The power delivery system of claim 1, wherein:
the primary winding is disposed on a transmission unit of the power delivery system and the secondary winding is disposed on a reception unit of the power delivery system, and
the reception unit is configured for movement relative to the transmission unit.

3. The power delivery system of claim 1, wherein the auxiliary component is configured to adjust the first voltage applied to the lower voltage component substantially independent of the modulated frequency of the modulated signal.

4. The power delivery system of claim 1, comprising a filter component disposed on a second circuit through which the first power is delivered via the modulated signal from the secondary winding to the high voltage component, wherein:
the filter component is configured to adjust a second voltage applied to the high voltage component, and
the second circuit is different than the first circuit.

5. The power delivery system of claim 4, wherein the filter component is configured to adjust the second voltage applied to the high voltage component based at least in part upon the modulated frequency of the modulated signal.

6. The power delivery system of claim 4, wherein the filter component comprises a frequency selective circuit.

7. The power delivery system of claim 6, wherein the frequency selective circuit comprises an LC circuit.

8. The power delivery system of claim 4, wherein the second circuit comprises a switch configured to electrically uncouple the high voltage component from the secondary winding.

9. The power delivery system of claim 1, comprising a modulation component configured to produce an original modulated signal comprising at least an original modulated amplitude and an original modulated frequency, wherein:
the original modulated signal is applied to the primary winding, and
the modulated signal is produced by the secondary winding derived from the original modulated signal.

10. The power delivery system of claim 1, comprising a frequency selective component disposed on a circuit through which the first power is delivered from the secondary winding to the high voltage component, wherein:
the frequency selective component is configured to adjust a voltage applied to the high voltage component based at least in part upon the modulated frequency of the modulated signal.

11. The power delivery system of claim 1, comprising:
a filter component configured to adjust a second voltage applied to the high voltage component.

12. The power delivery system of claim 11, wherein the filter component is configured to adjust the second voltage based at least in part upon the modulated frequency of the modulated signal.

13. The power delivery system of claim 12, wherein the auxiliary component is configured to adjust the first voltage substantially independent of the modulated frequency of the modulated signal.

14. The power delivery system of claim 1, wherein the high voltage component comprises an x-ray source configured to emit x-rays that are utilized to examine an object under examination.

15. A power delivery system, comprising:
an inverter disposed on a transmission unit of the power delivery system and configured to modulate a frequency and an amplitude of a signal to generate an original modulated signal having a modulated frequency and a modulated amplitude;
a transference component configured to derive a modulated signal from the original modulated signal, wherein the modulated signal comprises at least a frequency characteristic and an amplitude characteristic substantially consistent with the modulated frequency and the modulated amplitude of the original modulated signal;
an auxiliary rectifier coupled to a first circuit electrically coupling the transference component to a lower voltage component, wherein the auxiliary rectifier is configured to adjust a first voltage applied to the lower voltage component based at least in part upon the amplitude characteristic of the modulated signal; and
a filter component coupled to a second circuit electrically coupling the transference component to a high voltage component, wherein:
the filter component comprises a frequency selective circuit configured to adjust a second voltage applied to the high voltage component based at least in part upon the frequency characteristic of the modulated signal, and
the second voltage is different than the first voltage.

16. A power delivery system, comprising:
a rotary transformer comprising a primary winding and a secondary winding, wherein:
the rotary transformer is configured to deliver first power to a high voltage component and second power to a lower voltage component concurrently, and
the secondary winding is configured to produce a modulated signal comprising at least a modulated amplitude and a modulated frequency;
an auxiliary component disposed on a first circuit through which the second power is delivered via the modulated signal from the secondary winding to the lower voltage component, wherein the auxiliary component is configured to adjust a first voltage applied to the lower voltage component based at least in part upon the modulated amplitude of the modulated signal; and
a filter component disposed on a second circuit through which the first power is delivered via the modulated signal from the secondary winding to the high voltage component, wherein:
the filter component is configured to adjust a second voltage applied to the high voltage component,
the second circuit is different than the first circuit, and
the second circuit comprises a switch configured to electrically uncouple the high voltage component from the secondary winding.

17. The power delivery system of claim 16, wherein the auxiliary component is configured to adjust the first voltage applied to the lower voltage component substantially independent of the modulated frequency of the modulated signal.

18. The power delivery system of claim 16, wherein the filter component is configured to adjust the second voltage applied to the high voltage component based at least in part upon the modulated frequency of the modulated signal.

19. The power delivery system of claim 16, wherein:
the auxiliary component is configured to adjust the first voltage applied to the lower voltage component substantially independent of the modulated frequency of the modulated signal, and
the filter component is configured to adjust the second voltage applied to the high voltage component based at least in part upon the modulated frequency of the modulated signal.

20. The power delivery system of claim 16, comprising a modulation component configured to produce an original modulated signal comprising at least an original modulated amplitude and an original modulated frequency, wherein:
the original modulated signal is applied to the primary winding, and
the modulated signal is produced by the secondary winding derived from the original modulated signal.

* * * * *